United States Patent [19]

New et al.

[11] Patent Number: 4,677,104

[45] Date of Patent: Jun. 30, 1987

[54] ANTIPSYCHOTIC FUSED-RING PYRIDINYLPIPERAZINE DERIVATIVES

[75] Inventors: James S. New, Madison; Joseph P. Yevich, Southington, both of Conn.

[73] Assignee: Bristol-Myers Company, New York, N.Y.

[21] Appl. No.: 886,594

[22] Filed: Jul. 16, 1986

Related U.S. Application Data

[63] Continuation-in-part of Ser. No. 731,201, May 6, 1985, abandoned.

[51] Int. Cl.[4] .................. A61K 31/495; C07D 237/04
[52] U.S. Cl. ..................................... 514/222; 514/231; 514/234; 514/255; 544/58.2; 544/121; 544/230; 544/362
[58] Field of Search ............... 544/58.2, 121, 230, 544/362; 514/222, 231, 234, 255

[56] References Cited

U.S. PATENT DOCUMENTS

| | | | |
|---|---|---|---|
| 3,717,634 | 2/1973 | Wu et al. | 544/230 |
| 3,907,801 | 9/1975 | Wu et al. | 544/230 |
| 4,305,944 | 12/1981 | Temple et al. | 544/362 X |
| 4,361,565 | 11/1982 | Temple et al. | 544/364 X |
| 4,367,335 | 1/1982 | Temple et al. | 544/295 |
| 4,411,901 | 12/1983 | Temple et al. | 544/230 X |
| 4,452,799 | 6/1984 | Temple et al. | 544/230 X |
| 4,456,756 | 6/1984 | Temple et al. | 544/364 |
| 4,524,206 | 6/1985 | New et al. | 544/230 |
| 4,605,655 | 8/1986 | Yevich and Lobeck | 514/252 |
| 4,619,930 | 10/1986 | New et al. | 514/252 |

OTHER PUBLICATIONS

Wu et al., J. Med. Chem., vol. 15 (1972) pp. 477–479.
Anon, The Merck Index, 10th Edition (1983) p. 344.

*Primary Examiner*—Richard L. Raymond
*Attorney, Agent, or Firm*—Richard P. Ryan

[57] ABSTRACT

Disubstituted 1,4-piperazinyl derivatives are disclosed wherein one substituent is a bicyclic fused-ring furo-, pyrrolo-, cyclopentadieno-, or thieno-pyridine heterocyclic system and the second substituent is an alkylene chain attached to cyclic imide heterocycles, such as azaspiro[4.5]decanediones, dialkylglutarimides, thiazolidinediones, succinimides, and morpholine-2,6-diones; or a benzylic carbinol moiety. These compounds have potent antipsychotic and serotonin antagonist activities. 4-[4-[4-(4-Furo[3,2-c]pyridinyl)-1-piperazinyl]butyl]-3,5-morpholinedione is an example of a typical embodiment having selective antipsychotic activity.

43 Claims, No Drawings

ANTIPSYCHOTIC FUSED-RING PYRIDINYLPIPERAZINE DERIVATIVES

CROSS-REFERENCE TO RELATED APPLICATION

This is a continuation-in-part application of Ser. No. 731,201 filed May 6, 1985, now abandoned.

BACKGROUND OF THE INVENTION

This invention generally pertains to heterocyclic carbon compounds having drug and bio-affecting properties and to their preparation and use. In particular, the invention is concerned with 1,4-disubstituted piperazine derivatives wherein one substituent is a bicyclic fused-ring heterocyclic system comprising furo-, pyrrolo-, cyclo- pentadieno-, and thieno-pyridine ring systems; and the other is an alkylene chain, preferably a butylene chain, bearing a cyclic imide ring or a benzylic carbinol moiety at its terminus. Examples of types of these terminal moieties are depicted below;

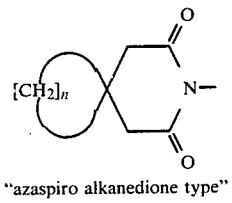

"azaspiro alkanedione type"

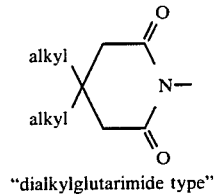

"dialkylglutarimide type"

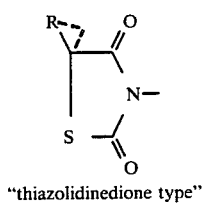

"thiazolidinedione type"

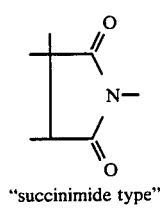

"succinimide type"

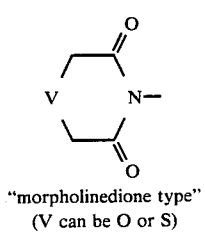

"morpholinedione type"
(V can be O or S)

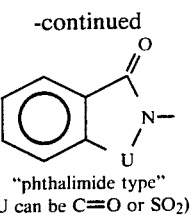

"phthalimide type"
(U can be C=O or $SO_2$)

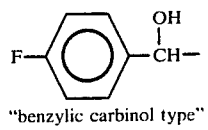

"benzylic carbinol type"

A considerable amount of related art has been generated over the past fifteen years, much of which has arisen from the research group of the Bristol-Myers Company. The pertinent related art comprising compounds with CNS activity may be viewed in light of the following general structural formula (1)

(1)

in which alk is an alkylene chain connnecting the piperazine ring with the cyclic imide group and B is a heterocyclic ring with optional substituents.

Wu, et al., U.S. Pat. Nos. 3,717,634 and 3,907,801 as well as a corresponding Wu, et al., publication—*J. Med. Chem.*, 15, 447–479 (1972)—describe various azaspiro[4.5]-decanedione psychotropic compounds wherein B represents various monocylic heterocycles such as pyridine, pyrimidine, or triazine, all with optional substituents.

Temple, Yevich and Lobeck in U.S. Pat. No. 4,305,944 disclose azaspiro[4.5]decanedione tranquilizing compounds wherein B is a 3-cyanopyridin-2-yl or 3-methoxypyridin-2-yl moiety.

Temple, Yevich and Lobeck report dialkylglutarimide tranquilizing compounds in U.S. Pat. No. 4,361,565 in which B is a 3-cyanopyridin-2-yl ring which may bear a second optional substituent.

Temple and Yeager in U.S. Pat. Nos. 4,367,335 and 4,456,756 disclose antipsychotic thiazolidinediones and spirothiazolidinediones wherein B is a 2-pyridinyl ring, either unsubstituted or containing a cyano substituent.

Temple and Yevich in U.S. Pat. Nos. 4,411,901, and 4,452,799 disclosed antipsychotic compounds with a variety of cyclic imide and benzylic carbinol moieties wherein B was either benzisothiazole or benzisoxazole ring systems.

Attention is also called to the following.

In U.S. Ser. No. 531,519, filed 9/12/83 and now U.S. Pat. No. 4,524,206, New and Yevich disclose and claim psychotropic succinimide and phthalimide-type compounds wherein B is a 2-pyrimidinyl ring. These compounds demonstrate antianxiety activity.

A series of antipsychotic 1-fluorophenylcarbonyl-, -carbinol-, -ketal-, propy-4-(2-pyrimidinyl)piperazines are disclosed by Yevich and Lobeck in U.S. Pat. No. 4,605,655.

Finally, New, Yevich and Lobeck in U.S. Pat. No. 4,619,930, disclose and claim a series of antipsychotic compounds which contain a variety of cyclic imide moieties and wherein B is a mono- or di-substituted pyridine ring system.

While the psychotropic compounds listed above are generally related to the compounds of the instant invention, they are nonetheless distinguishable thereof structurally on the basis of the B moiety of structural formula 1. Essentially, in the art compounds, B is usually a monocyclic heteroaryl ring with the only examples of bicyclic systems being fused benzo ring heterocyclics, i.e. benzisothiazole or benzisoxazole ring systems. This distinguishes these compounds from the compounds of the present invention in which B is comprised of different classes of fused heterocyclic rings, i.e. furo-, pyrrolo-, cyclopentadieno-, or thieno-pyridine ring systems. The instant compounds may also be distinguished pharmacologically on the basis of psychotropic properties and side effect profiles from the art compounds. In this regard, the compounds of the instant invention possess selective antipsychotic (neuroleptic) activity with serotonin antagonism, and, surprisingly, have low affinities for dopamine receptors which is in contrast to the prior art antipsychotic agents described, supra. In this regard, the instant compounds pharmacologically bear some semblance to the atypical standard neuroleptic agent, clozapine (2), cf: *The Merck Index*, 10th Edition (1983), page 344, and reference therein.

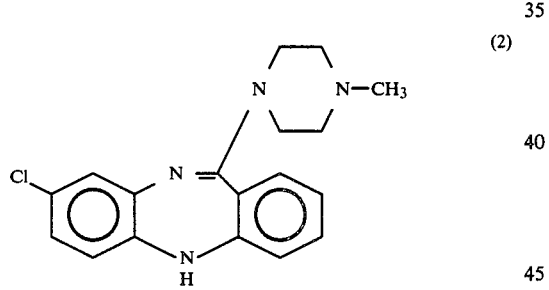
(2)

As can be seen, clozapine belongs to the dibenzodiazepine class of psychotropics which bear little structural relationship to the instant series of compounds. Additionally, the instant compounds appear to lack the potential for causing the adverse extrapyramidal symptomatology associated with the chronic administration of currently used antipsychotic agents. Further, selected compounds from the instant series have demonstrated in animal models, the ability to reverse catalepsy resulting from administration of trifluoperazine, a standard neuroleptic agent.

SUMMARY AND DETAILED DESCRIPTION OF THE INVENTION

In its broadcast aspect, the present invention is concerned with piperazinyl derivatives having neuroleptic (antipsychotic) properties characterized by a compound of Formula I and its pharmaceutically acceptable acid addition salts.

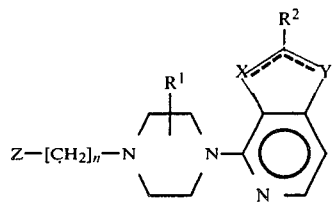

In Formula I, Z represents the following radicals:

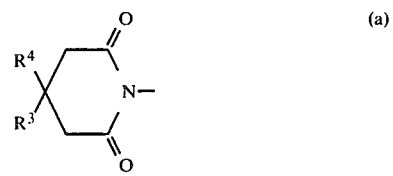
(a)

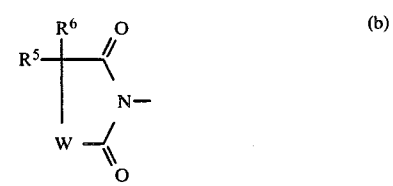
(b)

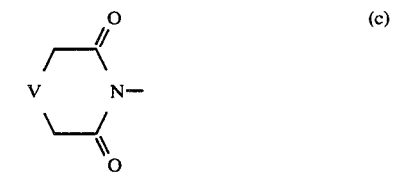
(c)

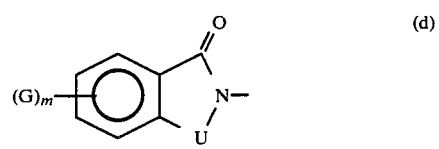
(d)

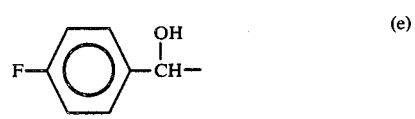
(e)

In radical (a) $R^3$ and $R^4$ are independently chosen from hydrogen, $C_{1-4}$ alkyl or $R^3$ and $R^4$ are taken together as a $C_3$ to $C_6$ alkylene chain. In radical (b) $R^5$ and $R^6$ are independently chosen from hydrogen, $C_{1-4}$ alkyl, and A-substituted phenyl with A being hydrogen or halogen, or $R^5$ and $R^6$ are taken together as a butylene chain; and W can be S (a sulfur atom) or $CH_2$ (a methylene group). In radical (c) V is an oxygen or sulfur atom. In radical (d) G is selected from hydrogen, $C_{1-4}$ alkyl, $C_{1-4}$ alkoxy or halogen, m is 1–4, and U is C=O or $SO_2$. Additionally, in Formula I: n is 2–4 with the proviso that when Z is (e), n is 3; $R^1$ is selected from hydrogen or $C_{1-4}$ alkyl; either X or Y is independently selected from $CH_2$, O, S, or $NR^7$ with the proviso that the other of X or Y must always be =CH—; $R^2$ is selected from hydrogen, $C_{1-4}$ alkyl, $C_{1-4}$ alkoxy, $C_{1-4}$ alkylthio, halogen, and hydroxyl; and $R^7$ is hydrogen or $C_{1-4}$ alkyl. The designation $C_{1-4}$ may also be defined by the term "lower".

Preferred classes of compounds are comprised of compounds of Formula I wherein Z can be the radicals (a); (b) with $R^5$ and $R^6$ being taken together as a butylene chain and with W being a sulfur atom; and (c) wherein V is an oxygen atom; and (e). For these preferred classes Y is either an oxygen or sulfur atom and X is methinyl (=CH—); n is 4, except when Z is (e) at which time n is 3; and $R^2$ is hydrogen.

These are two classes of most preferred compounds. For the class of compounds wherein Y is an oxygen atom, Z is either (a), (c) with V being and oxygen atom, an (e). For the class of compounds wherein Y is a sulfur atom, Z is either (a), (b), or (e).

The pharmaceutically acceptable acid addition salts of the invention are those in which the anion does not contribute significantly to the toxicity or pharmacological activity of the salt and, as such, they are the pharmacological equivalents of the bases of the Formula I compounds. They are generally preferred for medical usage. In some instances, they have physical properties which make them more desirable for pharmaceutical formulation. Such properties can be solubility, lack of hygroscopicity, compressibility with respect to tablet formation and compatibility with other ingredients with which the substance may be used for pharmaceutical purposes. The salts are routinely made by admixture of a Formula I base with a selected acid, preferably by contacting solutions employing an excess of commonly used inert solvents such as ether, benzene, ethanol, ethyl acetate, acetonitrile, and water. The salt form may also be prepared by any of the other standard methods detailed in the literature and available to any practitioner skilled in the art. Some examples of useful organic acids are the carboxylic acids such as maleic acid, acetic acid, tartaric acid, propionic acid, fumaric acid, isethionic acid, succinic acid, pamoic acid, cyclamic acid, pivalic acid, and the like; useful inorganic acid may be hydrohalide acids such as HCl, HBr, HI; sulfuric acids; phosphoric acids; and the like.

It is also to be understood that the present invention is considered to include any stereoisomers which may result when, for example, Z contains an asymmetric carbon; as in (e) and is possible in (b). Separation of the individual stereoisomers may be accomplished by application of various methods which are well known to practitioners in the art.

The compounds of the instant invention are useful pharmacological agents with psychotropic properties. In this regard, they exhibit selective central nervous system activity at non-toxic doses and are of particular interest as antipsychotic (neuroleptic) agents. As with other known antipsychotics, the compounds of Formula I evoke certain responses when studied in standard in vivo and in vitro pharmacological test systems which are known to correlate well with the relief of symptoms of acute and chronic psychosis in man.

For subclassification of the psychotropic activity and specificity of the instant compounds, state of the art in vitro central nervous system receptor binding methodology is employed. Certain compounds (commonly referred to as ligands) have been identified which preferentially bind to specific high affinity sites in brain tissue dealing with psychotropic activities or potential for side effects. Inhibition of radiolabeled ligand binding to such specific high affinity sites is considered a measure of a compound's ability to effect corresponding central nervous system function or to cause side effects in vivo. This principle is employed in tests, such as, for example, measuring inhibition of [$^3$H]spiperone binding which indicates significant dopamine receptor binding activity (cf: Burt, et al., *Molecular Pharmacology*, 12, 800 (1976); *Science*, 196, 326 (1977); Crease, et al., *Science*, 192, 481 (1976)).

Some of the more important binding tests employed are listed below in Table 1.

TABLE 1

Receptor Binding Tests

| Test No. | Putative Receptor Site | Ligand Used | Specific Binding Agent |
|---|---|---|---|
| 252A | Dopamine/spiperone/ neuroleptic | [$^3$H]Spiperone | D(+)-Butaclamol |
| 252B | Alpha-1 | [$^3$H]WB-4101 | Phentolamine |
| 252E | Serotonin Type 1 (5-HT$_1$) | [$^3$H]5-HT | 5-HT |
| 252I | Serotonin Type 2 (5-HT$_2$) | [$^3$H]Spiperone | D-Lysergide |

References:
252A - given supra.
252B - Crews, et al., Science, 202:322, 1978. Rosenblatt, et al., Brain Res., 160:186, 1979. U'Prichard, et al., Science, 199:197, 1978; Molec. Pharmacol., 13:454, 1977.
252E - Bennett and Snyder, Molec. Pharmacol., 12:373, 1976.
252I - Peroutka and Snyder, Molec. Pharmacol., 16:687, 1979.

Data derived from the above binding tests demonstrate that the family of compounds of the instant invention has modest to low affinity for dopaminergic receptors but much greater affinities for both serotonin $S_1$ and $S_2$ sites. These binding properties distinguish the instant compounds from the cited prior art compounds as well as most of the clinically useful antipsychotic agents now being used. In this regard, the instant compounds have some pharmacological properties in common with the atypical standard neuroleptic agent, clozapine, a dibenzodiazepine compound. The lack of dopaminergic binding affinities of the subject compounds is felt to relate to reduced liability to induce the unwanted extrapyramidal side effects common to most currently used antipsychotic agents.

Binding activity at the alpha-1 receptor (Test 252B) indicates that the compounds of the present invention will probably possess a sedating component of activity which is often desirable in the treatment of subgroups of psychotic patients.

The following in vivo test systems are conventionally used to classify and differentiate a psychotropic agent from a non-specific CNS depressant and to determine potential side-effect liabilities such as cataleptic activity.

TABLE 2

1. In Vivo Tests Used to Evaluate Formula I Compounds Conditioned Avoidance Response (CAR) - measure of a drug's tranquilizing activity as determined by its attenuation of avoidance response to electrical shock in trained fasted rats. cf: Albert, Pharmacologist, 4, 152 (1962); Wu, et al., J. Med. Chem., 12, 876–881 (1969).
2. Inhibition of Apomorphine-Induced (APO) Stereotypy - an assessment of blockade of dopaminergic activity in rats as measured by attenuation of the behavioral syndrome caused by the dopamine agonist, apomorphine. of: Janssen, et al., Arzneimittel. Forsch., 17, 841 (1966).
3. Catalepsy - drug-induced catalepsy in rats is predictive of potential extrapyramidal symptoms (EPS) in man. of: Costall, et al., Psychopharmacologia, 34, 233–241 (1974); Berkson, J. Amer. Statist. Assoc., 48, 565–599 (1953).
4. Catalepsy Reversal - measure of a drug's ability to reverse neuroleptic-induced catalepsy in the rat.

According to the pharmacological profile established by these in vivo tests, the instant compounds of Formula I have promising antipsychotic potential in that they are relatively potent in the CAR test, having oral $ED_{50}$ values <100 mg/kg body weight, and they effectively block apomorphine-induced stereotypy. This blockade of apomorphine-induced stereotypy may reflect dopamine antagonist activity and is accepted as a fairly specific screen for neuroleptic activity. The instant family of compounds may be considered to have selective antipsychotic activity inasmuch as antipsychotic activity is seen at doses which do not produce catalepsy. Not only are the instant compounds relatively inactive in catalepsy production but, even more significantly, preferred compounds of the invention demonstrate the ability to reverse neuroleptic-induced catalepsy with $ED_{50}$ values of <20 mg/kg, given orally. The significance of the effects of these compounds of the instant invention on catalepsy induction and reversal are better appreciated when one considers that antipsychotic agents as a class are known to produce extrapyramidal reactions. These unwanted extrapyramidal reactions represent a serious treatment liability and comprise acute torsion dystonia, akathesia, Parkinsonism, and tardive dyskinesia. Some representative in vivo biological data is tabulated in Table 6 (see further).

In summary of the foregoing discussion, the instant compounds have psychotropic properties particularly suited to their use as selective antipsychotic (neuroleptic) agents with little potential for movement disorder side effects. Thus, another aspect of the instant invention concerns a process for ameliorating a psychotic state in a mammal in need of such treatment which comprises systemic administration to such mammal of an effective dose of a Formula I compound or a pharmaceutically acceptable acid addition salt thereof.

The administration and dosage regimen of compounds of Formula I is considered to be done in the same manner as for the reference compound clozapine, cf: *The Merck Index*, 10th Edition, (1983), page 344, and references therein. Although the dosage and dosage regimen must in each case be carefully adjusted, utilizing sound professional judgment and considering the age, weight and condition of the recipient, the route of administration and the nature and gravity of the illness, generally the daily dose will be from about 0.05 to about 10 mg/kg, preferably, 0.1 to 2 mg/kg, when administered parenterally; and from about 1 to about 50 mg/kg, preferably 2 to 30 mg/kg, when administered orally. In some instances, a sufficient therapeutic effect can be obtained at lower doses while in others, larger doses will be required. The term "systemic administration" as used herein refers to oral, rectal, and parenteral, i.e., intramuscular, intravenous, and subcutaneous routes. Generally, it will be found that when a compound of the present invention is administered orally, which is the preferred route, a larger quantity of the active agent is required to produce the same effect as a smaller quantity when given parenterally. In accordance with good clinical practice, it is preferred to administer the instant compounds at a concentration level that will produce effective antipsychotic (neuroleptic) effects without causing any harmful or untoward side effects.

Therapeutically, the instant compounds are generally given as pharmaceutical compositions comprised of an effective antipsychotic amount of a compound of Formula I or a pharmaceutically acceptable acid addition salt thereof and a pharmaceutically acceptable carrier. Pharmaceutical compositions for effecting such treatment will contain a major or minor amount, e.g. from 95 to 0.5% of at least one compound of the present invention in combination with a pharmaceutical carrier, the carrier comprising one or more solids, semi-solid, or liquid diluent, filler, and formulation adjuvant which is non-toxic, inert and pharmaceutically acceptable. Such pharmaceutical compositions are preferably in dosage unit forms; i.e., physically discrete units containing a pre-determined amount of the drug corresponding to a fraction of multiple of the dose which is calculated to produce the desired therapeutic response. The dosage units can contain one, two, three, four or more single doses; or alternatively, one-half, one-third, or one-fourth of a single dose. A single dose preferably contains an amount sufficient to produce the desired therapeutic effect upon administration at one application of one or more dosage units according to the pre-determined dosage regimen, usually a whole, half, third, or quarter of a daily dosage administered once, twice, three or four times a day. Other therapeutic agents can also be present. Pharmaceutical compositions which provide from about 1 to 500 mg of the active ingredient per unit dose are preferred and are conventionally prepared as tablets, lozenges, capsules, powders, aqueous or oily suspensions, syrups, elixirs, and aqueous solutions. Preferred oral compositions are in the form of tablets or capsules and may contain conventional excipients such as binding agents (e.g. syrup, acacia, gelatin, sorbitol, tragacanth, or polyvinylpyrrolidone), fillers (e.g. lactose, sugar, maize-starch, calcium phosphate, sorbitol or glycine), lubricants (e.g. magnesium stearate, talc, polyethylene glycol or silica), disintegrants (e.g. starch), and wetting agents (e.g. sodium lauryl sulfate). Solutions or suspensions of a Formula I compound with conventional pharmaceutical vehicles are employed for parenteral compositions such as an aqueous solution for intravenous injection or an oily suspension for intramuscular injection. Such compositions having the desired clarity, stability and adaptability for parenteral use are obtained by dissolving from 0.1% to 10% by weight of the active compound in water or a vehicle consisting of a polyhydric aliphatic alcohol such as glycerine, propylene glycol, and polyethylene glycols or mixtures thereof. The polyethylene glycols consist of a mixture of non-volatile, usually liquid, polyethylene glycols which are soluble in both water and organic liquids and which have molecular weights of from about 200 to 1500.

The compounds of Formula I wherein Z is comprised of the radicals (a-e) of the instant invention are obtained by procedures involving alkylation of piperazinyl or "imide" intermediates analogous to methods described by Wu, et al., patents, supra., or Temple, et al., patents, supra., all incorporated herein in entirety by reference. These methods may be incorporated into a unitary process which is employed for preparation of the compounds of Formula I. The methods may be adapted to variation in order to produce other compounds embraced by this invention but not specifically disclosed. Further, variations of the methods to produce the same compounds in somewhat different fashion will also be evident to one skilled in the art. Certain examples will be given for specific illustration.

Unitary Process

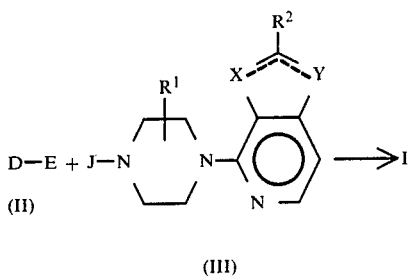

In this scheme, $R^1$, $R^2$, X and Y have the same meanings as previously assigned to them in Formula I. The symbol D is either the divalent structures related to radicals (a-d) as shown below in partial structures (a'-d') or D is the radical (e') also shown below.

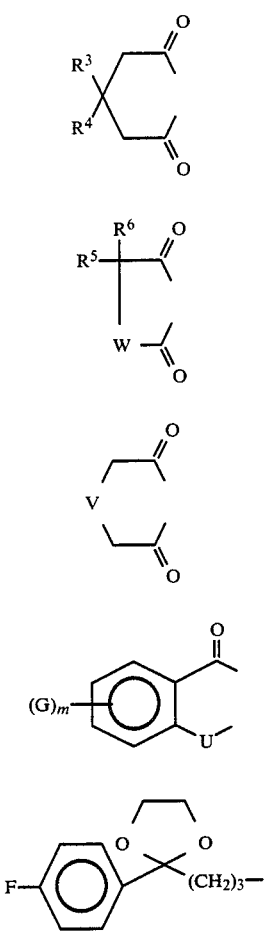

In radicals (a'-e') all symbols have the same meanings as previously assigned hereinabove. The symbol "E" in the above scheme can be O; N—H; or N—$(CH_2)_n$—Q. The symbol "n" is as previously defined and "Q" refers to a suitable displacement group such as chloride, bromide, iodide, sulfate, phosphate, tosylate, or mesylate. The symbol "J" can be $H_2N$—$(CH_2)_n$—; Q—$(CH_2)_n$—;

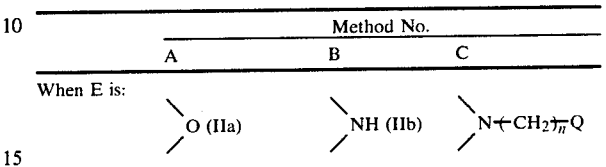

or H—. The relationship between E and J is

| | Method No. | | |
|---|---|---|---|
| | A | B | C |
| When E is: | \O (IIa) / | \NH (IIb) / | \N—$(CH_2\frac{}{n})$Q (IIc) / |
| Then J is: | $H_2N$—$(CH_2)_n$— (IIIa) | X—$(CH_2)_n$— (IIIb) or | H— (IIIc) |
| | | 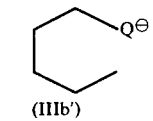 (IIIb') | |

Method A

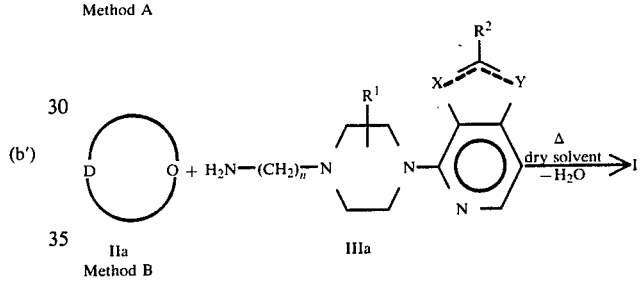

Method B (1)

(2)

(IIIb' is a special case wherein n is fixed at 4)
Method C (the preferred method)

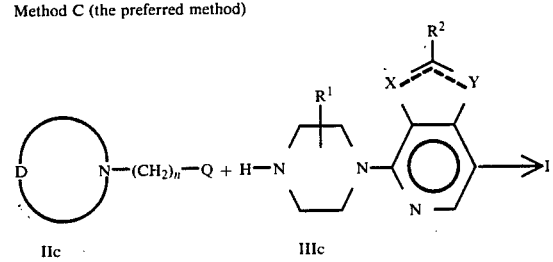

The condensation in Method A is carried out by refluxing the reactants in a dry, inert reaction medium such as pyridine or xylene. For Methods B and C the process is carried out under reaction conditions suitable for the preparation of tertiary amines by alkylation of secondary amines. The reactants are heated in a suitable organic liquid at temperatures of about 60° to about 100° C. in the presence of an acid binding agent. Benzene, dimethylformamide, ethanol, acetonitrile, toluene and n-butyl alcohol are preferred examples of the organic liquid reaction media. The preferred acid binding agent is potassium carbonate, but other inorganic and tertiary organic bases may be employed including other alkali and alkaline earth metal carbonates, bicarbonates, or hydrides, and the tertiary amines. All three methods have been adequately described in the patent references referred to hereinabove as being incorporated in entirety by reference. For the compounds of the instant invention, Method C is the preferred synthetic process. The required IIc intermediates were synthesized according to methods given in the incorporated reference patents.

For preparation of the Formula I products wherein Z is (e), the following adaptation of Method C is employed.

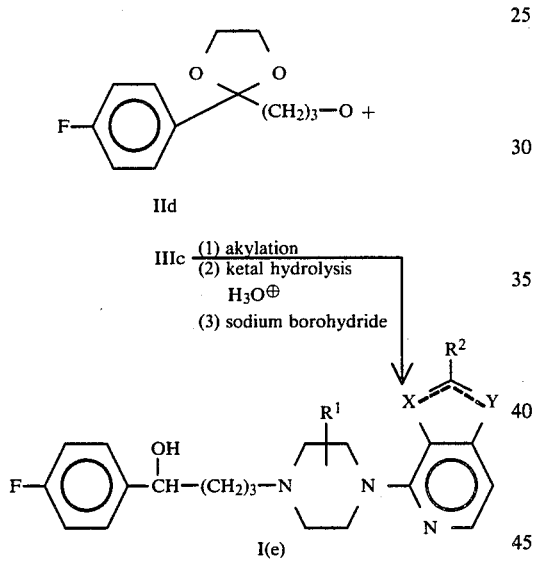

As an example of a method variation to produce the compounds of Formula I somewhat differently a Z-substituted alkyl piperazine (IV) can be reacted with an appropriate fused bicyclic pyridine system (V) to yield a product of Formula I, e.g.

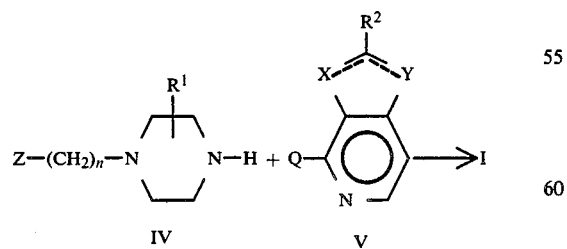

To summarize the foregoing, there is described a process for the preparation of a compound of Formula I this process comprises selection of a process from the group of processes consisting of (a) reacting an intermediate of Formula IIa

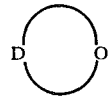
IIa wherein the symbol "D" is the divalent structure of Formulas a'-d'

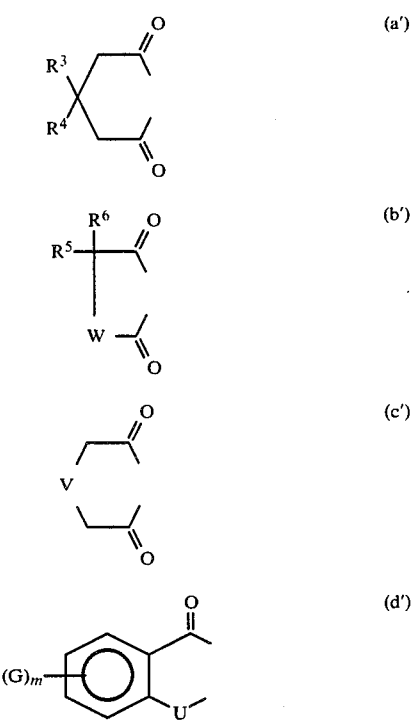

with an intermediate of Formula IIIa

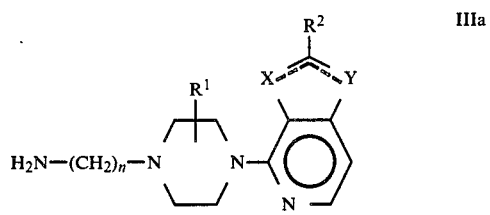
IIIa wherein $R^1$, $R^2$, n, X and Y are as previously defined, to give a product of Formula I;

(b) reacting a compound of Formula IIb

IIb with an intermediate compound of Formula IIIb

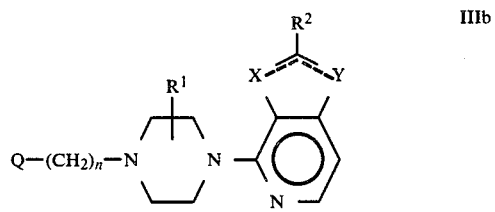
IIIb wherein Q is a suitable displacement group such as chloride, bromide, iodide, sulfate, phosphate, tosylate, or mesylate, and D, R¹, R², n, X and Y are as previously defined, to give a product of Formula I;

(c) reacting a compound of Formula IIb with an intermediate compound of Formula IIIb'

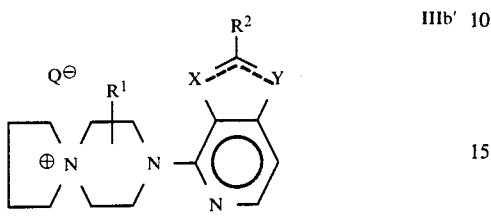

wherein Q, R¹, R², X and Y are as previously defined, to yield a product of Formula I wherein n is fixed at the integer 4;

(d) reacting a compound of Formula IIc

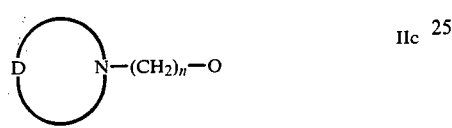

with an intermediate compound of Formula IIIc

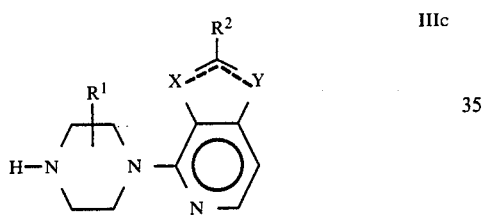

wherein D, n, Q, R¹, R², X, and Y are as previously defined, to yield a product of Formula I;

(e) reacting a compound of Formula IV

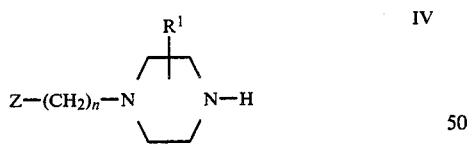

with an intermediate compound of Formula V

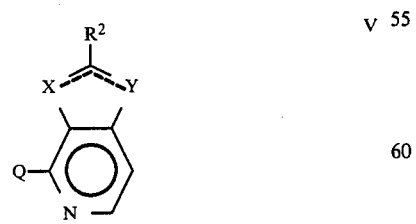

wherein Z, n, R¹, R², Q, X, and Y are as previously defined to give a product of Formula I; and (f)
(1) reacting a compound of Formula IId

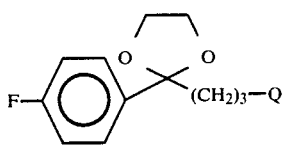

with an intermediate compound of Formula IIIc to give a compound of Formula If;

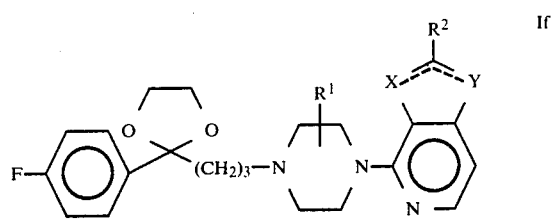

(2) hydrolyzing If in acidic media to provide a compound of Formula Ig; and

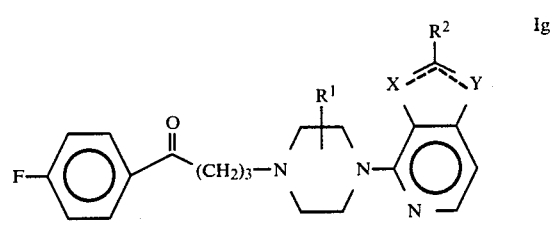

(3) reducing the compound of Formula Ig with sodium borohydride to give the product Ie.

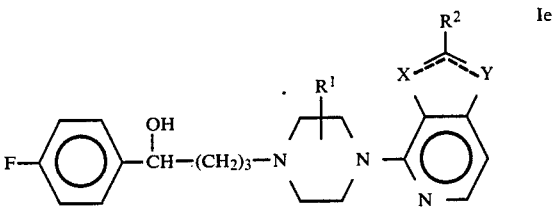

The intermediate compounds of Formulas II or IV are adequately described in the incorporated above-cited patent references and references therein; as well as several Formula II compounds being commercially available. The bicyclic pyridinylpiperazine intermediate compounds of Formula III, as well as the starting bicyclic heterocycles (V) themselves, are either commercially available, found in the chemical literature, or described herein. Methods used for the synthhesis of Formula III intermediates are illustrated in Scheme I.

Scheme I
Synthesis of the Bicyclic Intermediates III.

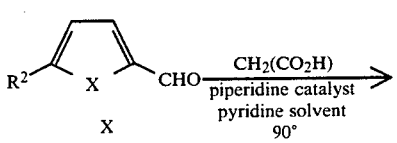

-continued
Scheme I
Synthesis of the Bicyclic Intermediates III.

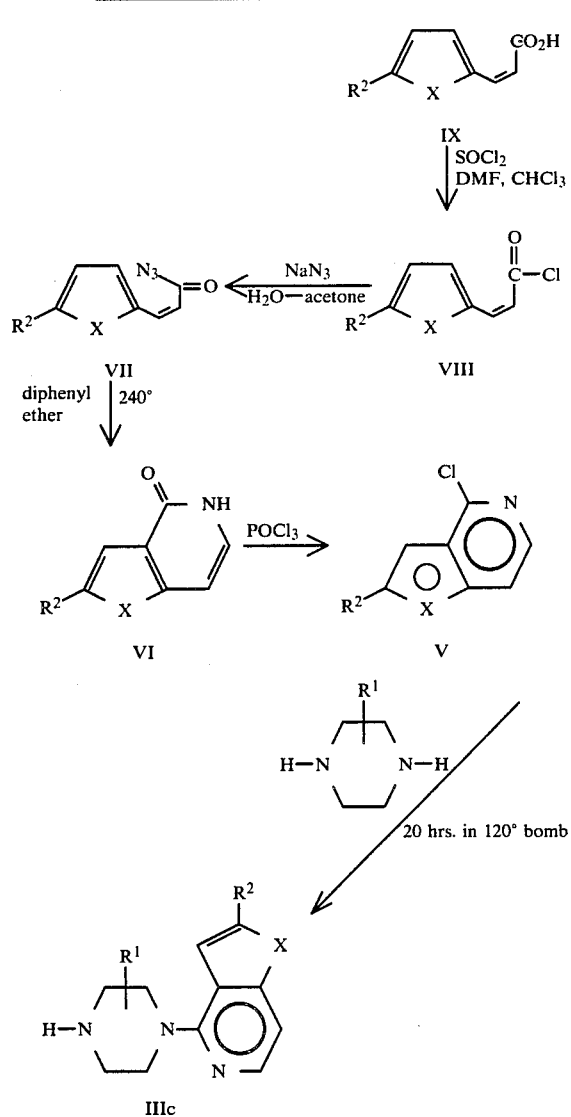

In Scheme I, synthesis of the furo-, pyrrolo-, cyclopentadieno-, or thieno-pyridine ring systems is accomplished starting with a carboxaldehyde intermediate of Formula X. The 2-carboxaldehyde intermediate is shown in Scheme I and ultimately gives rise to the intermediate IIIc as shown in Scheme I. If the 3-carboxaldehyde intermediate X' is used in Scheme I, the resultant product is the "reverse" isomer IIIc'.

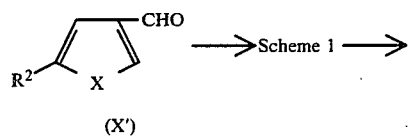

-continued

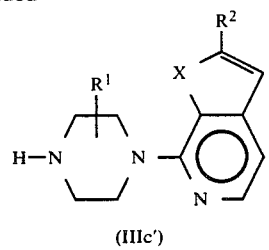

Generic structure III (wherein J=H) of the unitary process, supra. generally depicts the structures of both intermediate IIIc and IIIc'.

In Scheme I, the requisite starting carboxaldehyde can either be obtained commercially or by simple synthesis, e.g. Vilsmeier-Haack Formylation of an N-alkylpyrrole, utilizing methods readily available in the chemical literature and familiar to one skilled in the chemical arts. Condensation of intermediate X with malonic acid at 100° C. usually in pyridine as a solvent with piperidine as a catalyst, for approximately 12 hours, followed by a short reflux period to enhance decarboxylation, yields the corresponding acrylic acid intermediates of structure IX. Chlorination of the Formula IX acids with thionyl chloride in chloroform and a catalytic amount of dimethylformamide affords the acid chloride derivatives of structure VIII, which are not purified but may be used in crude form in the preparation of the acid azides of Formula VII. These acid azides are prepared either in a biphasic mixture of acetone in water at 5° through the agency of sodium azide or with trimethylsilylazide in refluxing benzene. Unpurified preparations of the acid azides of Formula VII in methylene chloride solutions are added in portions to either diphenyl ether or diphenylmethane and heated to 230° facilitating the Curtius-type rearrangement via isocyanates which immediately cyclize to the fused 6-5 bicyclic intermediates of Formula VI. Chlorination of VI is achieved using phosphorous oxychloride or a phosphorus pentachloridephosphorus oxychloride mixture to generate the chloro substituted heterocyclic of Formula V. Reaction of V with an excess of an appropriate piperazine in a bomb at 120°-140° C. for varying periods of time affords the desired piperazine intermediate IIIc. This general synthesis of intermediates of Formula IIIc has been reported previously (cf: Eloy, et al., *Bull. Soc. Chim. Belges.*, 79, 301 (1976); *J. Heterocyclic Chem.*, No. 8, 57 (1971); *Helv. Chim. Acta.*, 53, 645 (1970)). Introduction of the substituent $R^2$ may be done either by its incorporation in the starting compound X or by introduction later in the scheme, e.g. metalation of V (X=S, $R^2$=H) with t-butyllithium and subsequent reaction with dimethyldisulfide to give an intermediate of Formula V wherein $R^2$=$SCH_3$.

Utilization of the intermediate compounds of Formula III in the unitary process described above and employing Methods A-C, preferably Method C, results in synthesis of the antipsychotic compounds of Formula I.

DESCRIPTION OF SPECIFIC EMBODIMENTS

The compounds which constitute this invention and their methods of preparation will appear more fully from a consideration of the following examples which are given for the purpose of illustration only and are not to be construed as limiting the invention in sphere or scope. All temperatures are understood to be in degrees C. when not specified. The nuclear magnetic resonance (NMR) spectral characteristics refer to chemical shifts (δ) expressed in parts per million (ppm) versus tetramethylsilane (TMS) as reference standard. The relative area reported for the various shifts in the proton (PMR) spectral data corresponds to the number of hydrogen atoms of a particular functional type in the molecule. The nature of the shift as to multiplicity is reported as broad singlet (bs), singlet (s), multiplet (m), doublet (d), doublet of doublets (dd), triplet (t), or quartet (q). Abbreviations employed are DMSO-$d_6$ (perdeuterodimethylsulfoxide), CDCl$_3$ (deuterochloroform) and are otherwise conventional. The infrared (IR) spectral descriptions include only absorption wave numbers (cm$^{-1}$) having functional group identification value. The IR determinations were employed using potassium bromide (KBr) as diluent. All compounds gave satisfactory elemental analysis.

Synthesis of Intermediates of Formula IIIc

The following representative examples of chemical intermediates of Formulas V-X illustrate synthesis of the key intermediate IIIc, which can be further converted using known reactions as in the cited patents, into other synthetic intermediates such as IIIa or IIIb.

EXAMPLE 1

N-Methylpyrrole-2-carboxaldehyde (X)

A stirred mixture of N-methylpyrrole (10 g, 0.12 mole) in dichloroethane (80 mL) and dimethylformamide (11.3 g, 0.15 mole) was treated dropwise at 5° with phosphorus oxychloride (23.6 g, 0.15 mole) which led to an exothermic reaction with formation of a precipitate. Stirring was continued for an additional 15 minutes and the precipitate was collected by filtration, suspended in 3N NaOH solution (300 mL) and extracted with chloroform (3×100 mL). The chloroform portions were combined, dried (MgSO$_4$), filtered, and concentrated in vacuo affording 6.1 g (49%) of a dark oil, b.p. 87°-90° at 22 Torr., whose NMR was consistent with the assigned structure. This intermediate was generally used unpurified in the next step of Scheme 1.

EXAMPLE 2

3-(2-Thieno)acrylic Acid (IX)

A mixture of 2-thiophenecarboxaldehyde (100 g, 0.89 mole); malonic acid (182.5 g, 1.70 mole); pyridine (446 mL); and piperidine (8.9 mL) was heated at 100° for 12 hours. The reaction solution was then refluxed for 20 minutes and allowed to cool, whereupon it was poured into water (1000 mL) and the resulting aqueous mixture was acidified with conc. HCl. The resulting off-white precipitate was collected by filtration and recrystallized from ethanol-water (1:1) yielding 109 g (80%) of product, m.p. 145°-148°.

EXAMPLE 3

3-(2-Thieno)acryloyl Chloride (VIII)

A stirred suspension of 3-(2-thieno)acrylic acid (118.9 g, 0.77 mole) and dimethylformamide (12 mL) in chloroform (600 mL), was treated dropwise with thionyl chloride (110.1 g, 0.93 mole) at room temperature. The reaction was then refluxed for 2 hours, cooled and concentrated in vacuo to a brown oil which solidifed upon further standing to 131 g (99%) of a low melting solid, which was used without further purification.

EXAMPLE 4

4-Oxo-4,5-dihydrothieno[3,2-c]pyridine (VI)

A stirred suspension of sodium azide (168.6 g, 2.6 mole) in a mixture of p-dioxane (400 mL) and water (400 mL) was treated dropwise with a solution of 3-(2-thieno)acryloyl chloride (223.9 g, 1.3 mole) in dioxane at 5°. The dioxane layer resulting from this biphasic mixture was isolated, concentrated in vacuo, dissolved in methylene chloride (500 mL), dried (MgSO$_4$), and filtered. This methylene chloride filtrate was added dropwise to refluxing diphenylether (400 mL) in a 3-neck flask equipped with two air condensers. The solution was refluxed an additional hour, cooled, and concentrated in vacuo to a dark syrup which was crystallized in acetonitrile to afford a brown solid which was collected by filtration. Recrystallization of the solid from water (650 mL) yielded 106 g (54%) of a pale yellow solid, m.p. 213°-214°.

EXAMPLE 5

4-Chlorothieno[3,2-c]pyridine (V)

Finely divided 4-oxo-4,5-dihydrothieno[3,2-c]pyridine (105.6 g, 0.69 mole) was stirred while being treated dropwise with phosphorus oxychloride (321.5 g, 2.1 mole) at 0°. The reaction mixture was then refluxed for 2.5 hours, cooled, and cautiously poured onto crushed ice (1000 mL). The resulting solution was stirred for 30 minutes and extracted with dichloromethane (3×400 mL). The organic portions were combined, dried (MgSO$_4$), filtered, and concentrated in vacuo to a solid which was recrystallized from acetonitrile (400 mL) affording 101 g (85%) of light yellow solid, m.p. 91°.

EXAMPLE 6

4-(1-Piperazinyl)thieno[3,2-c]pyridine (IIIc)

A mixture of 4-chlorothieno[3,2-c]pyridine (22.7 g, 0.13 mole) and piperazine (57.7 g, 0.67 mole) were heated in a bomb with a minimum amount of ethanol (50 mL) at 120° for 24 hours. The reaction was cooled, partitioned between dichloromethane and water, and the organic layer was isolated, dried (MgSO$_4$), filtered, and concentrated in vacuo to an oil. Flash chromatography (methylene chloride-10% methanol-1% ammonium hydroxide) of this material gave 16 g (54%) of a golden oil. Treatment of an ethanol solution of the oil with ethanolic HCl followed by recrystallization from ethanol gave the hydrochloride salt as off-white crystals, m.p. 275°-283°.

EXAMPLE 7

Synthesis of 7-(1-Piperazinyl)thieno[2,3-c]pyridine (IIIc')

The synthesis of this compound was accomplished with the same sequence of reactions as used to prepare IIIc, except that the starting material (X) is 3-thiophenecarboxaldehyde. The multiple step preparation of the positional isomer IIIc' was complicated, however, in that the Curtius-type rearrangement reaction (Example 4) gave the desired VI intermediate compound in low yield as the major product of this reaction was a sym-triazine by-product which resulted from trimerization of the isocyanate intermediate. Nonetheless, application of the reactions outlined in Scheme 1 resulted in production of the IIIc' product, which was a brown gum and was used without further purification.

By appropriate modification of the Scheme 1 reaction sequence and the various synthetic reactions exemplified above, additional IIIc compounds may be synthesized. Some additional representative IIIc compounds are shown in Table 3.

TABLE 3

Additional Formula IIIc Compounds

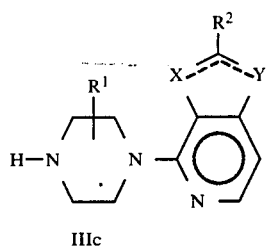

IIIc

| Example | $R^1$ | $R^2$ | X | Y | m.p. (°C.) |
|---|---|---|---|---|---|
| 8 | H | H | CH | N—CH$_3$ | |
| 9 | H | H | CH | O | >250 |
| 10 | H | H | CH | CH$_2$ | |
| 11 | H | H | N—CH$_3$ | CH | |
| 12 | H | H | O | CH | |
| 13 | CH$_3$ | H | CH | S | |
| 14 | H | CH$_3$ | CH | N—CH$_3$ | |
| 15 | CH$_3$ | OCH$_3$ | CH | O | |
| 16 | H | SCH$_3$ | CH | S | 203–205 (.HCl.H$_2$O) |
| 17 | CH$_3$ | Cl | O | CH | |
| 18 | H | Br | S | CH | |
| 19 | H | OH | CH | CH$_2$ | |
| 20 | H | C$_2$H$_5$ | CH | S | |
| 21 | H | H | S | CH | |
| 22 | H | SCH$_3$ | CH | S | |

Synthesis of Formula I Compounds

EXAMPLE 23

General Synthesis

Synthesis of the product compounds of Formula I was accomplished by alkylation of appropriate halo-substituted imide derivatives (IIc), where D is (a'–d') and E is N-(CH$_2$)$_n$-Q with Q being halide; or the fluorophenylbutyrophenone derivative (IId) with an appropriate IIIc intermediate compound in refluxing acetonitrile, with three equivalents of potassium carbonate present. The carbinol derivatives were generated by sodium borohydride reduction of the corresponding butyrophenone. Reaction times for the alkylation varied from 5 to 72 hours and the resulting products were usually subjected to flash chromatography in an ethanol-chlorofrom mixture for purification. The Formula I products were usually formulated as the hydrochloride salt for testing.

EXAMPLE 24

4,4-Dimethyl-1-[4-[4-(thieno[3,2-c]pyridin-4-yl)-1-piperazinyl]butyl]-2,6-piperidinedione A mixture of 4-(1-piperazinyl)thieno[3,2-c]pyridine (IIIc; 2.79 g, 0.012 mole), N-4-bromobutyl)-3-dimethylglutarimide (3.3 g, 0.012 mole) and potassium carbonate (3.3 g, 0.024 mole) was refluxed in acetonitrile (150 mL) for 24 hour. The reaction mixture was filtered, concentrated in vacuo and partitioned between dichloromethane and water. The organic layer was isolated, dried (MgSO$_4$) and concentrated in vacuo to a gold oil which was flash chromatographed (5% ethanol-chloroform). The chromatographed material was dissolved in acetonitrile and treated with ethanolic HCl to yield 1.3 g (24% yield) of the hydrochloride salt, m.p. 195°–197°.

Anal. Calcd. for C$_{22}$H$_{30}$N$_4$O$_2$S.HCl: C, 58.59; H, 6.93; N, 12.42. Found: C, 58.64; H, 7.02; N, 12.72.

PMR (DMSO-d$_6$): 1.08 (6, s); 1.71 (4, m); 2.60 (4, s); 3.40 (10, m); 4.00 (2, m); 7.65 (2, m); 7.87 (1, m); 8.08 (1, d [5.0 Hz]); 11.75 (1, bs).

IR (KBr): 715, 965, 1425, 1535, 1670, 1720, 2580, 2960 cm$^{-1}$.

EXAMPLE 25

4-[4-[4-(4-Furo[3,2-c]pyridinyl)-1-piperazinyl]butyl]-3,5-morpholinedione

A mixture of 4-(1-piperazinyl)furo[3,2-c]pyridine (4.5 g, 0.022 mole), 4-(4-bromobutyl)-3,5-morpholinedione (5.5 g, 0.022 mole), and potassium carbonate (9.1 g, 0.066 mole) was refluxed in acetonitrile for 24 hours. The reaction mixture was filtered, concentrated in vacuo, and partitioned between dichloromethane and water. The organic layer was isolated, dried (MgSO$_4$), and concentrated in vacuo to a yellow oil which was flash chromatographed. The appropriate chromatographic fractions were combined, concentrated in vacuo, and crystallized from isopropanol yielding 6.2 g (69%) of the free base, m.p. 109°–110°.

Anal. Calcd. for C$_{19}$H$_{24}$N$_4$O$_4$: C, 61.28; H, 6.50; N, 15.04. Found: C, 60.98; H, 6.60; N, 15.19.

PMR (CDCl$_3$): 1.60 (4, m); 2.40 (2, m); 2.57 (4, m); 3.74 (6, m); 4.31 (4, s); 6.78 (1, d [2.0 Hz]); 6.89 (1, d [5.8 Hz]); 7.49 (1, d [2.0 Hz]); 8.01 (1, d [5.8 Hz]).

IR (KBr): 760, 780, 1250, 1285, 1440, 1460, 1570, 1595, 1690, 1735, 2830 cm$^{-1}$.

Using the methodology referred to above, or alternate synthetic methods disclosed in the referenced and incorporated patents, a wide assortment of Formula I products may be provided. Tables 4 and 5 contain a listing of additional representative Formula I products. Table 6 contains in vivo biological data for representative compounds of Formula I.

TABLE 4
Formula I Products
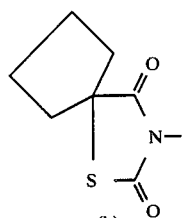
| Ex. No. | Z | n | R¹ | R² | X | Y | Formula[a] | m.p. (°C.) |
|---|---|---|---|---|---|---|---|---|
| 26 | 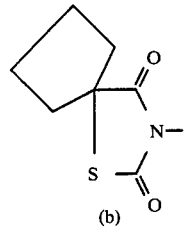 (b) | 4 | H | H | CH | S | $C_{22}H_{22}N_4O_2O_2 \cdot 1.4HCl$ | 180–182 |
| 27 | (e) | 3 | H | H | CH | S | $C_{21}H_{24}FN_3OS$ | 115–118 |
| 28 | 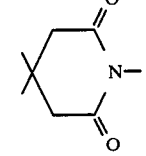 (b) | 4 | H | Br | CH | S | $C_{22}H_{27}BrN_4O_2S_2 \cdot HCl$ | 203–205 |
| 29 | 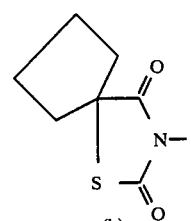 (a) | 4 | H | Br | CH | S | $C_{22}H_{29}BrN_4O_2S \cdot HCl \cdot 0.5H_2O$ | 216–219 |
| 30 | 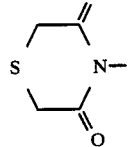 (b) | 4 | H | CH₃ | CH | S | $C_{23}H_{30}N_4O_2S_2 \cdot HCl$ | 195–197 |
| 31 | 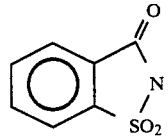 (c) | 4 | H | H | CH | S | $C_{19}H_{24}N_4O_2S_2 \cdot 1.1C_7H_8O_3S \cdot 0.5H_2O$ | 186–188 |
| 32 |  (d) | 4 | H | H | CH | S | $C_{22}H_{24}N_4O_3S_2 \cdot HCl$ | 229–230 |

TABLE 4-continued
Formula I Products
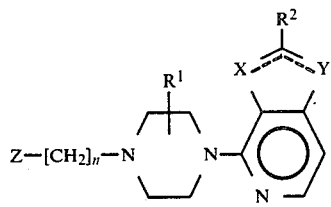
| Ex. No. | Z | n | R¹ | R² | X | Y | Formula[a] | m.p. (°C.) |
|---|---|---|---|---|---|---|---|---|
| 34 | (d) | 4 | H | H | CH | S | $C_{23}H_{24}N_4O_2S \cdot HCl \cdot 0.5H_2O$ | 226-227 |
| 36 | (b) | 4 | H | H | S | CH | $C_{22}H_{28}N_4O_2S_2 \cdot 2HCl \cdot 1.8H_2O$ | 120-122 |
| 37 | (b) | 4 | H | H | CH | O | $C_{22}H_{28}N_4O_3S \cdot 2HCl \cdot C_2H_6O$ | 251-253 |
| 38 | (a) | 4 | H | H | CH | O | $C_{22}H_{30}N_4O_3 \cdot 1.4HCl$ | >250 |
| 39 | (e) | 3 | H | H | CH | O | $C_{21}H_{24}FN_3O_2 \cdot HCl$ | 205-207 |
| 40 | (b) | 4 | H | CH₃ | CH | O | $C_{23}H_{30}N_4O_3S \cdot 1.2HCl$ | 176-177 |

TABLE 4-continued

Formula I Products

Z—[CH₂]ₙ—N(piperazine with R¹)—N—(pyridine)—fused ring with X=Y, R²

| Ex. No. | Z | n | R¹ | R² | X | Y | Formula(a) | m.p. (°C.) |
|---|---|---|---|---|---|---|---|---|
| 41 | 4,4-dimethyl-glutarimide (a) | 4 | H | CH₃ | CH | O | C₂₃H₃₂N₄O₃·1.2HCl·0.5H₂O | 321–233 |
| 42 | thiomorpholine-3,5-dione (c) | 4 | H | H | CH | O | C₁₉H₂₄N₄O₃S·2HCl·0.5H₂O | 245–250 |
| 43 | (e) | 3 | H | CH₃ | CH | O | C₂₂H₂₆FN₃O₂·HCl* | 121–122 |
| 44 | thiomorpholine-3,5-dione (c) | 4 | H | H | CH | S | C₁₉H₂₄N₄O₃S·0.5H₂O | 114–115 |
| 45 | 4-methylglutarimide (a) | 4 | H | H | CH | S | C₂₁H₂₈N₄O₂S·HCl | 173–175 |
| 46 | glutarimide (a) | 4 | H | H | CH | S | C₂₀H₂₆N₄O₂S·HCl | 199–201 |
| 47 | spirocyclobutyl-methylthiazolidinedione | 4 | H | H | CH | NMe | C₂₃H₃₁N₅O₂S·2HCl·1.6H₂O | 148–150 |

TABLE 4-continued
Formula I Products

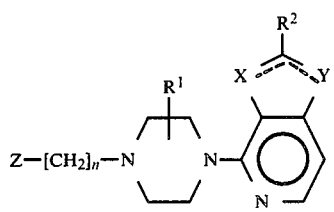

| Ex. No. | Z | n | R¹ | R² | X | Y | Formula[a] | m.p. (°C.) |
|---|---|---|---|---|---|---|---|---|
| 48 | (structure) (c) | 4 | H | H | CH | NMe | $C_{20}H_{27}N_5O_3 \cdot 2.3HCl \cdot 0.4H_2O$ | 144–146 |
| 49 | (structure) (a) | 4 | H | H | CH | NMe | $C_{23}H_{33}N_5O_2 \cdot 2.1HCl \cdot 2.6H_2O$ | 192–194 |
| 58 | (structure) | 4 | H | H | CH | S | $C_{20}H_{26}N_4O_2S \cdot HCl$ | 199–201 |
| 59 | (structure) | 4 | H | H | CH | S | $C_{21}H_{28}N_4O_2S \cdot HCl$ | 173–175 |

[a] C, H, and N elemental analyses were all with ±0.4% of theoretical values for the formulas given.

TABLE 5
Additional Formula I Products

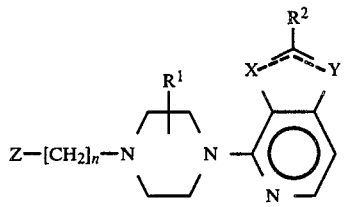

| Ex. No. | Z | n | R¹ | R² | X | Y |
|---|---|---|---|---|---|---|
| 33 | (structure) | 4 | H | H | CH | S |

TABLE 5-continued
Additional Formula I Products

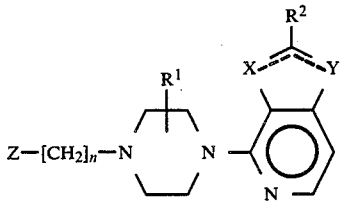

| Ex. No. | Z | n | R¹ | R² | X | Y |
|---|---|---|---|---|---|---|
| 35 | (structure) | 4 | CH₃ | H | CH | S |

TABLE 5-continued

Additional Formula I Products

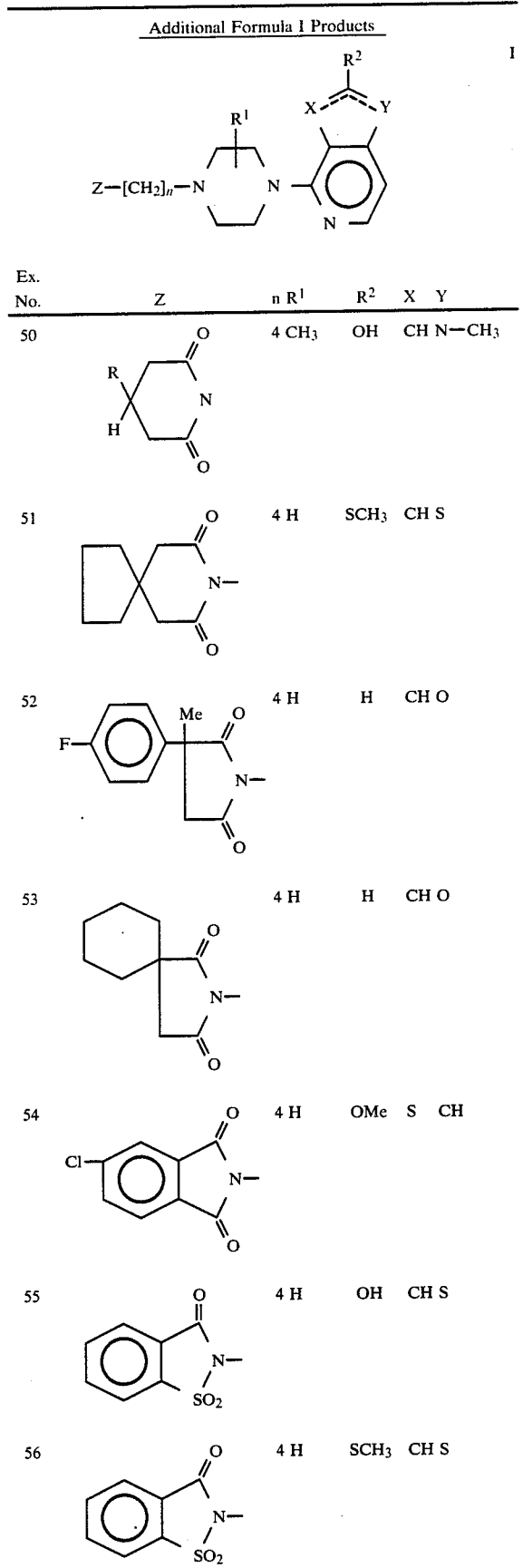

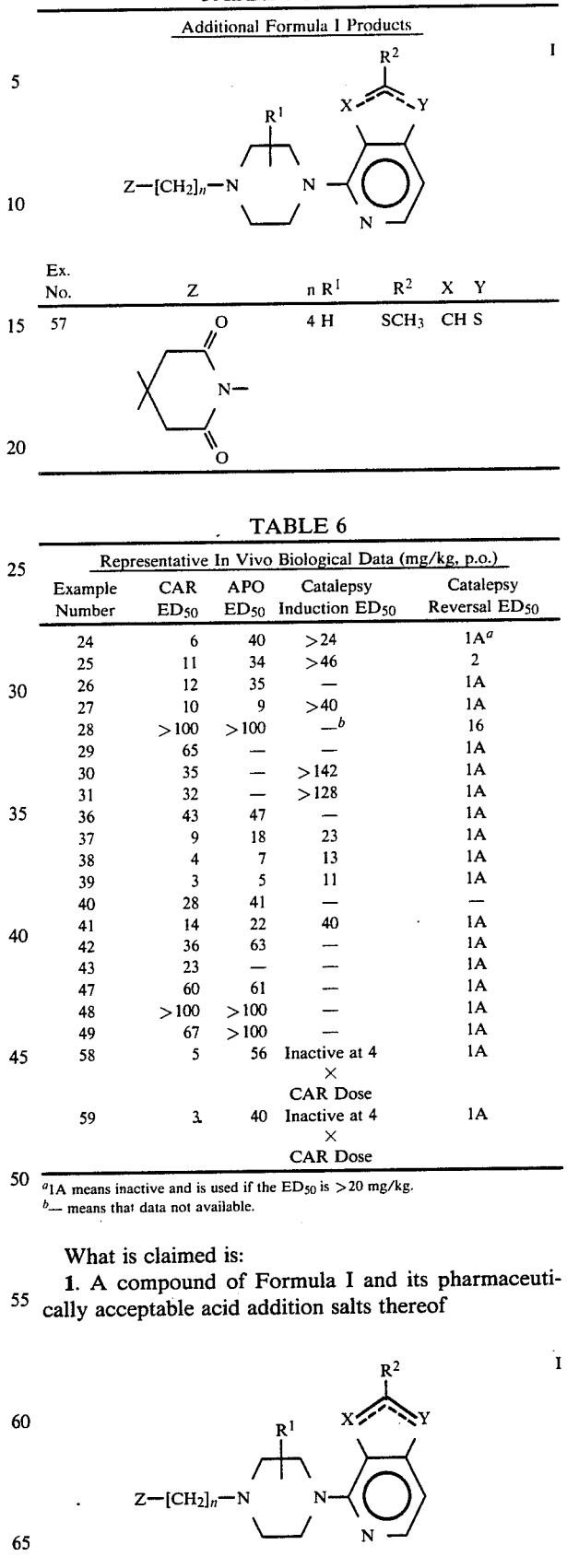

| Ex. No. | Z | n | R[1] | R[2] | X | Y |
|---|---|---|---|---|---|---|
| 57 | (3,3-dimethylglutarimide) | 4 | H | SCH$_3$ | CH | S |

TABLE 6
Representative In Vivo Biological Data (mg/kg, p.o.)

| Example Number | CAR ED$_{50}$ | APO ED$_{50}$ | Catalepsy Induction ED$_{50}$ | Catalepsy Reversal ED$_{50}$ |
|---|---|---|---|---|
| 24 | 6 | 40 | >24 | 1A[a] |
| 25 | 11 | 34 | >46 | 2 |
| 26 | 12 | 35 | — | 1A |
| 27 | 10 | 9 | >40 | 1A |
| 28 | >100 | >100 | —[b] | 16 |
| 29 | 65 | — | — | 1A |
| 30 | 35 | — | >142 | 1A |
| 31 | 32 | — | >128 | 1A |
| 36 | 43 | 47 | — | 1A |
| 37 | 9 | 18 | 23 | 1A |
| 38 | 4 | 7 | 13 | 1A |
| 39 | 3 | 5 | 11 | 1A |
| 40 | 28 | 41 | — | — |
| 41 | 14 | 22 | 40 | 1A |
| 42 | 36 | 63 | — | 1A |
| 43 | 23 | — | — | 1A |
| 47 | 60 | 61 | — | 1A |
| 48 | >100 | >100 | — | 1A |
| 49 | 67 | >100 | — | 1A |
| 58 | 5 | 56 | Inactive at 4 × CAR Dose | 1A |
| 59 | 3 | 40 | Inactive at 4 × CAR Dose | 1A |

[a] 1A means inactive and is used if the ED$_{50}$ is >20 mg/kg.
[b] — means that data not available.

What is claimed is:

1. A compound of Formula I and its pharmaceutically acceptable acid addition salts thereof $$\text{Z—[CH}_2\text{]}_n\text{—N} \quad \text{(structure I)}$$

wherein

Z is selected from among the following radicals:

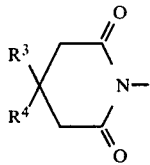

where R³ and R⁴ are independently chosen from hydrogen, lower alkyl or may be taken together as a $C_3$-$C_6$ alkylene chain;

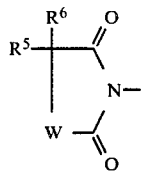

in which R⁵ and R⁶ are independently chosen from hydrogen, lower alkyl, and A-substituted phenyl with A being hydrogen or halogen, or R⁵ and R⁶ are taken together as a butylene chain, and W can be S or $CH_2$;

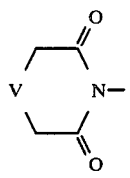

in which V is O or S;

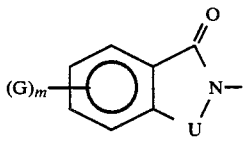

in which G is selected from hydrogen, lower alkyl, lower alkoxy, or halogen, m is the integer 1–4, and U is C═O or $SO_2$; and

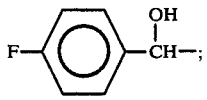

n is the integer 2–4 with the proviso that when Z is (e), n is 3; either

X or Y is independently selected from $CH_2$, O, S, or $NR^7$ with the proviso that the other X or Y must always be ═CH—;

R¹ and R⁷ are independently selected from hydrogen or lower alkyl; and

R² is selected from hydrogen, lower alkyl, lower alkoxy, lower alkylthio, halogen, and hydroxyl.

2. The compound of claim 1 wherein Z is the radical (a).

3. The compound of claim 1 wherein Z is the radical (b).

4. The compound of claim 1 wherein Z is the radical (c).

5. The compound of claim 1 wherein Z is the radical (d).

6. The compound of claim 1 wherein Z is the radical (e).

7. The compound of claim 1 wherein Y is an oxygen atom.

8. The compound of claim 1 wherein Y is a sulfur atom.

9. The compound of claim 3 wherein R⁵ and R⁶ are taken together as a butylene chain and W is sulfur.

10. The compound of claim 4 wherein V is an oxygen atom.

11. The compound of claim 7 wherein Z is the radical (a), (c) or (e).

12. The compound of claim 8 wherein Z is the radical (a), (b), or (e).

13. The compound of claim 2, 1-[4-[4-(furo[3,2-c]pyridin-4-yl)-1-piperazinyl]butyl]-4,4-dimethyl-2,6-piperidinedione.

14. The compound of claim 2, 4,4-dimethyl-1-[4-[4-[(2-methylfuro[3,2-c]pyridine-4-yl)-1-piperazinyl]-butyl]2,6-piperidinedione.

15. The compound of claim 2, 4,4-dimethyl-1[4-[4-(thieno[3,2-c]pyridin-4-yl)-1-piperazinyl]butyl]-2,6-piperidinedione.

16. The compound of claim 2, 4,4-dimethyl-1-[4-[4-(1-methyl-1H-pyrrolo[3,2-c]pyridin-4-yl)-1-piperazinyl]-butyl]-2,6-piperidinedione.

17. The compound of claim 2, 4,4-dimethyl-1-[4-[4-(2-bromothieno[3,2-c]pyridin-4-yl)-1-piperazinyl]butyl]-2,6-piperidinedione.

18. The compound of claim 2, 1-[4-[4-(thieno[3,2-c]pyridin-4-yl-1-piperazinyl]butyl]1,6-piperidinedione.

19. The compound of claim 2, 4-methyl-1-[4-[4-(thieno[3,2-c]pyridin-4-yl)-1-piperazinyl]butyl]-2,6-piperidinedione.

20. The compound of claim 3, 3-[4-[4-(furo[3,2-c]pyridin-4-yl)-1-piperazinyl]butyl]-1-thia-3-azaspiro[4.4]nonane-2,4-dione.

21. The compound of claim 3, 3-[4-[4-(2-methylfuro[3,2-c]pyridin-4-yl)-1-piperazinyl]butyl]-1-thia-3-azaspiro[4.4]nonane-2,4-dione.

22. The compound of claim 3, 3-[4-[4-(thieno[3,2-c]pyridin-4-yl)-1-piperazinyl]butyl]-1-thia-3-azaspiro[4,4]nonane-2,4-dione.

23. The compound of claim 3, 3-[4-[4-(1-methylpyrrolo[3,2-c]pyridin-4-yl)-1-piperazinyl]butyl]-1-thia-3-azaspiro[4.4]nonan-2,4-dione.

24. The compound of claim 3, 3-[4-[4-(2-bromothieno[3,2-c]pyridin-4-yl)-1-piperazinyl]butyl]-1-thia-3-azaspiro[4.4]nonane-2,4-dione.

25. The compound of claim 3, 3-[4-[4-(2-methylthieno[3,2-c]pyridin-4-yl)-1-piperazinyl]butyl]-1-thia-3-azaspiro[4.4]nonane-2,4-dione.

26. The compound of claim 1, 3-[4-[4-(thieno[2,3-c]pyridin-7-yl)-1-piperazinyl]butyl]-1-thia-3-azaspiro[4.4]nonane-2,4-dione.

27. The compound of claim 4, 4-[4-[4-(4-furo[3,2-c]pyridinyl)-1-piperazinyl]butyl]-3,5-morpholinedione.

28. The compound of claim 4, 4-[4-[4-(1-methyl-1H-pyrrolo[3,2-c]pyridin-4-yl)-1-piperazinyl]butyl]3,5-morpholinedione.

29. The compound of claim 4, 4-[4-[4-(4-thieno[3,2-c]pyridinyl)-1-piperazinyl]butyl]-3,5-thiomorpholinedione.

30. The compound of claim 4, 4-[4-[4-(4-thieno[3,2-c]pyridinyl)-1-piperazinyl]butyl]-3,5-morpholinedione.

31. The compound of claim 5, 2-[4-[4-(thieno[3,2-c]pyridin-4-yl-1-piperazinyl]butyl]-1H-isoindole-1,3-(2H)-dione.

32. The compound of claim 5, 2-[4-[4-(thieno[3,2-c]pyridin-4-yl)-1-piperazinyl]butyl]-1,2-benzisothiazol-3(2H)-one 1,1-dioxide.

33. The compound of claim 6, α-(4-fluorophenyl)4-(furo[3,2-c]pyridin-4-yl)-1-piperazinebutanol.

34. The compound of claim 6, α-(4-fluorophenyl)-4-(2-methylfuro[3,2-c]pyridin-4-yl)-2-piperazinebutanol.

35. The compound of claim 6, α-(4-fluorophenyl)-4-(thieno[3,2-c]pyridin-4-yl)-1-piperazinebutanol.

36. The compound of claim 2, 1-[4-[4-(thieno[3,2-c]pyridin-4-yl)-1-piperazinyl]butyl]-2,6-piperidinedione.

37. The compound of claim 2, 4-methyl-1-[4-[4-(thieno[3,2-c]pyridin-4-yl)-1-piperazinyl]butyl]-2,6-piperidinedione.

38. The method for ameliorating an undesirable psychotic state in a mammal comprising administration to said mammal of an effective antipsychotic amount of a compound claimed in claim 1.

39. The method of claim 38 comprising the administration of 4,4-dimethyl-1-[4-[4-(thieno[3,2-c]pyridin-4-yl)-1-piperazinyl]butyl]-2,6-piperidinedione.

40. The method of claim 38 comprising administration of 3-[4-[4-(1-methylpyrrolo[3,2-c]pyridin-4-yl)-1-piperazinyl]butyl]-1-thia-3-azaspiro[4.4]nonane-2,4-dione.

41. A pharmaceutical composition in dosage unit form suitable for systemic administration to a mammalian host comprising a pharmaceutical carrier and from about 1–500 mg. of an active compound selected from the compounds claimed in claim 1.

42. The pharmaceutical composition of claim 41 wherein the active compound is 4,4-dimethyl-1-[4-[4-(thieno[3,2-c]pyridin-4yl)-1-piperazinyl]butyl]-2,6-piperidinedione.

43. The pharmaceutical composition of claim 41 wherein the active compound is 3-[4-[4-(1-methylpyrrolo[3,2-c]pyridin-4-yl)-1-piperazinyl]butyl]-1-thia-3-azaspiro[4.4]nonane-2,4-dione.

* * * * *